(12) United States Patent
Matic et al.

(10) Patent No.: US 7,883,894 B2
(45) Date of Patent: Feb. 8, 2011

(54) PROCESS FOR THE REVERSIBLE FUNCTIONAL INACTIVATION OF THE MISMATCH REPAIR SYSTEM

(75) Inventors: Ivan Matic, Boulogne-Billancourt (FR); Miroslav Radman, Gentilly (FR)

(73) Assignee: Mixis France S.A., Paris (FR)

( * ) Notice: Subject to any disclaimer, the term of this patent is extended or adjusted under 35 U.S.C. 154(b) by 523 days.

(21) Appl. No.: 10/503,226

(22) PCT Filed: Dec. 19, 2002

(86) PCT No.: PCT/EP02/14533

§ 371 (c)(1), (2), (4) Date: Apr. 21, 2005

(87) PCT Pub. No.: WO03/064667

PCT Pub. Date: Aug. 7, 2003

(65) Prior Publication Data

US 2005/0176149 A1 Aug. 11, 2005

(30) Foreign Application Priority Data

Jan. 31, 2002 (EP) ................................. 02002337

(51) Int. Cl.
*C12N 1/00* (2006.01)
*C12N 1/20* (2006.01)
*C12N 1/38* (2006.01)
*C12N 15/74* (2006.01)
*C12N 15/63* (2006.01)

(52) U.S. Cl. ........................ 435/471; 435/477; 435/243; 435/252.4; 536/23.1; 536/23.4

(58) Field of Classification Search ........................ None
See application file for complete search history.

(56) References Cited

U.S. PATENT DOCUMENTS

| | | | |
|---|---|---|---|
| 5,912,119 A | 6/1999 | Radman et al. | |
| 5,965,415 A | 10/1999 | Radman et al. | |
| 2002/0088021 A1* | 7/2002 | Mahajan | ..................... 800/278 |

FOREIGN PATENT DOCUMENTS

| | | |
|---|---|---|
| WO | WO-90/07576 | 7/1990 |
| WO | WO-91/09954 | 7/1991 |
| WO | WO-93/02216 | 2/1993 |
| WO | WO-97/05268 | 2/1997 |

OTHER PUBLICATIONS

Glcikman and Radman, *Escherichia coli* mutator mutants deficient in mehtylation-instructed DNA mismatch correction, PNAS, 1980, vol. 77 (2), pp. 1063-1067.*
Negishi et al, Saturation of DNA Mismatch Repair and Error Catastrophe by a Base Analogue in *Escherichia coli*, Genetics 161: 1363-1371 (Aug. 2002).*
Griffith et al, Modern Genetic Analysis, Ch 9, The Genetics of Bacteria and Phage, downloaded Feb. 8, 2009, pp. 1-6.*
Palmer et al, 2-Aminopurine Induces Spindle CEII Morphology in MM14 Myoblasts in the Absence of Differentiation Signals, Experimental Cell Research, 1997, vol. 230, pp. 262-274.*
Cupples, C. G., et al.; "A set of LAC-Z Mutations in *Escherichia coli* that Allow Rapid Detection of Specific Frameshift Mutations"; Genetics; vol. 1(2); 1990; pp. 275-280.
Georgina Macintyre, et al.; "The Vsr endonuclease of *Escherichia coli*: An efficient DNA repair enzyme and a potent mutagen."; Journal of Bacteriology; vol. 179(19); 1997; pp. 6048-6052.
Prudhomme, M., et al.; "Mismatch Repair Genes of *Streptococcus pneumoniae*: Hexa Confers a Mutator Phenotype in *Escherichia coli* by Negative Complementation"; Journal of Bacteriology, Washington DC, US; vol. 173(22); Nov. 1991; pp. 7196-9193.
Rayssiguier, C., et al.; "The Barrier to Recombination Between *Escherichia coli* and *Salmonella typhimurium* is Disrupted in Mismatch-Repair Mutants"; Nature; vol. 342; Nov. 1989; pp. 396-401.
Kowalczykowski, S. et al., "Biochemistry of Homologous Recombination in *Eschericha coli*", Microbiological Reviews, 58(3):401-465 (1994).
Sagi, D. et al., "High fidelity of RecA-catalyzed recombination: a watchdog of genetic diversity", Nucleic Acids Research, 34(18):5021-5031 (2006).
Shen, P. et al., "Homologous recombination in *Escherichia coli*: Dependence on Substrate Length and Homology", Genetics, 112:441-451 (Mar. 1986).
Bianchi, M. and Radding, C.M., "Insertions, Deletions and Mismatches in Heteroduplex DNA Made by RecA Protein", Cell, 35:511-520 (Dec. 1983 (Part I)).

* cited by examiner

*Primary Examiner*—Maria Marvich
(74) *Attorney, Agent, or Firm*—Dickstein Shapiro LLP

(57) ABSTRACT

The present invention relates to a process for allowing homologous recombination between non-identical DNA sequences of an organism and various applications thereof.

12 Claims, 2 Drawing Sheets

PROCESS FOR THE REVERSIBLE FUNCTIONAL INACTIVATION OF THE MISMATCH REPAIR SYSTEM

Figure 1:
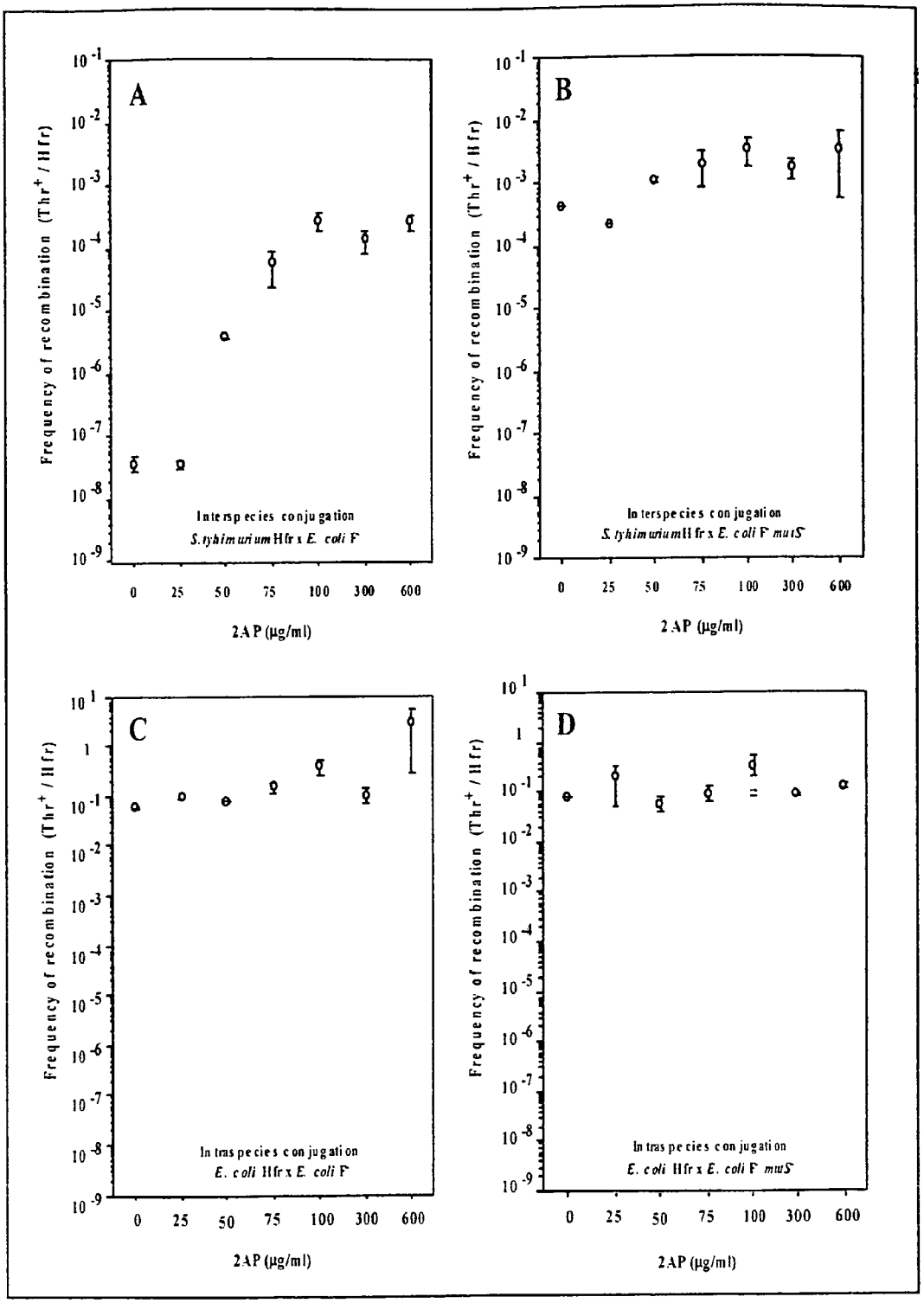

The present invention relates to a process for the reversible functional inactivation of the mismatch repair system in an organism and various applications thereof. In particular the present invention relates to a process for the in vivo recombination of non-identical nucleotide sequences. The present invention also relates to a process for the production of hybrid organisms produced by recombination in vivo of different organisms, species or genera. The present invention also relates to a process for the in vivo production of hybrid genes and proteins encoded thereby.

Evolution is the selection of the fittest variants produced by mutation and recombination. Random mutation produces new alleles whereas genetic recombination produces new combinations of pre-existing alleles. This property of genetic recombination improves the effectiveness of mutagenesis because it allows for association of multiple adaptive mutations, as well as for their separation from much more frequent deleterious mutations. The efficiency of genetic recombination depends on the DNA sequence identity shared by the two recombining molecules and on the cellular enzymatic systems involved in recombination and its editing (Radman and Wagner, 1993; Matic et al., 1996). Recombination between DNAs differing by well-spaced point mutations (sequence polymorphism) is reduced or inhibited. Crosses between different bacterial strains and species show that the recombination frequency decreases exponentially with increasing of the genomic sequence divergence (Vulic et al., 1997). Pairing of non-identical DNA sequences results in generation of mismatched heteroduplex molecules. Mismatched base pairs are recognised by the components of the mismatch repair system (MRS) that acts as an inhibitor of recombination between non-identical DNA sequences (Rayssiguier et al., 1989; Shen and Huang, 1989; Worth Jr. et al., 1994; Zahrt et al., 1994; Matic et al., 1995).

This function of MRS plays an important role in the maintenance of the structural integrity of chromosomes and the genetic isolation between different bacterial species. For example, the inactivation of MRS genes increases 10-15-fold the frequency of chromosomal duplications resulting from recombination between E. coli rhsA and rhsB loci (only 0.9% divergent) (Petit et al., 1991) and about $10^3$-fold gene conversion between S. enterica (serovar Typhimurium) tufA and tufB genes (about 1% divergent) (Abdulkarim and Hughes, 1996). MRS also controls the conjugational and transductional recombination between divergent strains and species (Rayssiguier et al., 1989; Zahrt et al., 1994; Matic et al., 1995; Vulic et al., 1997). Even low divergence is sufficient to impede recombination. For example, transductional recombination between two serovars (Typhimurium and Typhi) of S. enterica, whose genomes differ only 1-2% at DNA sequence level, increase $10^2$-$10^3$-fold in MRS deficient genetic backgrounds (Zahrt et al., 1994).

Three genes have been shown to be required specifically for MRS in E. coli: mutS, mutL and mutH (Friedberg et al., 1995). The inactivation of different MRS genes has a distinct and characteristic effect on the interspecies recombination (Rayssiguier et al., 1989; Stambuk and Radman, 1998; Denamur et al., 2000). The strongest hyper-recombination effect is observed upon inactivation of mutS and mutL genes, as described for instance in U.S. Pat. No. 5,956,415 and U.S. Pat. No. 5,912,119. On the contrary, the overproduction of MutS and MutL proteins severely reduces the recombination frequency even between bacterial strains with very low genomic divergence (Vulic et al., 1997). Thus, by modifying the activity of MRS it is possible to disrupt or establish genetic barriers between different bacterial species.

When generating genetic diversity by recombination, one of the major problems with recombination in a MRS proficient background is that DNA sequence divergence restricts recombination events to the genomic regions of the highest sequence similarity. Consequently, the majority of recombinants are highly unstable merodiploids, often generated by an unequal crossover between ribosomal RNA (rrn) operons, which are usually almost identical between related bacterial species. The inactivation of MRS allows not only higher yield of interspecies recombinants, but also higher diversity and higher stability of hybrids. The potential applications of this strategy, that allows creation of interspecific mosaic genomes, are multiple in fundamental research, biotechnology, genetic engineering and medicine. By allowing recombination of entire genomes, the mosaic genomes with new combinations of genes and operons (even with mosaic genes and operons) can be obtained.

However, every time a new bacterial strain or species is used for recombination, the mutS or mutL gene must be knocked-out. This can be very difficult when those genes are not identified and/or when the genetic tools for gene knock-out have not been developed for a given species. Besides, the inactivations of MRS genes increase the mutation rates $10^2$-$10^3$-fold, which can be undesirable once a desired construction has been obtained. The alternative would be the inhibition/saturation of MRS using some other approaches. For example, (i) MRS can be saturated by excessive DNA replication errors in E. coli strains carrying a defective dnaQ gene coding for proof-reading activity of replicative DNA polymerase (PolIII) (Schaaper and Radman, 1989). (ii) The efficiency of the MRS has also been shown to decrease as a result of titration of the mismatch repair proteins in cells containing mismatches in retron-encoded multicopy single-stranded DNA (Maas et al., 1996). U.S. Pat. No. 5,965,415 and U.S. Pat. No. 5,912,119 describe processes for intergeneric and interspecific recombination, wherein the MRS is transitorily inactivated by mutations in the MRS genes and subsequent restoration of the MRS using a correction mutant or by saturating the MRS by the introduction of nucleotide sequences comprising a large number of mismatches. However, in the latter case the enzymatic component of the MRS is apparently destroyed and functional reactivation of the MRS requires resynthesis of the repair enzymes. (iii) Over-expression of MRS proteins from non-related bacterial species can also inhibit E. coli MRS and results in increased mutagenesis (Prudhomme et al., 1991). However, although all the above mentioned methods for the inhibition/saturation of MRS do not require inactivation of the MRS genes, additional modification of the cells is necessary in order to reduce the mutation and recombination rates once the required recombinants are obtained.

Thus, the technical problem underlying the present invention is to provide a simple method to inactivate or at least to considerably reduce the MRS activity of an organism in order to increase the recombination rate between partially homologous, i.e. non-identical or divergent nucleotide sequences in the organism, whereby avoiding subsequent additional modification of the treated cells to reduce the mutation and recombination rates.

The present invention solves the technical problem by providing a process for the reversible, i.e. transitory, functional inactivation of the mismatch repair system (MRS) in an organism which process comprises subjecting the organism to an agent capable of partially or completely inhibiting the mismatch repair system of the organism in an amount and for a period of time sufficient to reversibly increase the recombination rate between the non-identical nucleotide sequences, in particular DNA sequences, present in the organism and, in a preferred embodiment, subsequently removing the agent from the organism.

Thus, the present invention provides means to reversibly inactivate the MRS which in turn allows a number of useful applications, such as increasing the recombination rate of non-identical nucleotide sequences. Hence, the present invention provides also processes to increase the recombination rate in an organism and processes to mutagenise an organism whereby the MRS is reversibly inactivated as described herein.

In one aspect of the present invention the process of the present invention provides the advantage that by reversibly inactivating the MRS of an organism, the recombination rate between non-identical DNA sequences present in the organism can be reversibly increased, avoiding the need of subsequent manipulations of the treated cells and maintaining the MRS genetically and constantly intact.

In the context of the present invention, non-identical or divergent nucleotides, in particular DNA-sequences, particularly preferred double-stranded DNA sequences present in an organism comprise first sequences, i.e. autologous nucleotides, in particular DNA sequences, present in the organism, preferably prior to uptake of second sequences, and said second sequences introduced into this organism for instance by natural sex, conjugation, transduction, artificial cell fusion or any other means known in the art such as chemical, electrical, biolistic or physical treatments. Of course both the first and the second sequences may be introduced simultaneously into the organism. These introduced second sequences are non-identical, that means not completely identical or homologous to the second sequences. In particular, these partially homologous sequences have a significant portion of mismatched bases, for instance up to 30%. The partially homologous sequences are capable of activating the MRS, if the MRS is functional and not inactivated, inhibited or saturated. The introduced sequences are allowed to recombine with the autologous DNA sequences present in the organism due to the reversibly inactivated mismatch repair system. Once the recombination has taken place, the agent used according to the present invention may be removed so that the mismatch repair system may regain its original functionality. One advantage of the transient inhibition or saturation of the MRS is that, after recombination, the obtained hybrid cells do not have constitutively high mutation rates due to a permanent inactivation of the MRS genes.

In a particularly preferred embodiment of the present invention the non-identical DNA sequences are present in the form of genes, operons, gene clusters, chromosomes, plasmids and/or genomes. These DNA sequences may be naturally occurring or artificially manipulated DNA sequences.

The present invention allows a very significant increase of the efficiency of recombination between non-identical DNA sequences that is normally inhibited by the mismatch repair system. The present invention may advantageously be used to facilitate the generation of new biodiversity at the level of individual genes or operons, as well of entire genomes. Chemical inhibition of the MRS in order to increase the efficiency of the recombination between non-identical DNA sequences according to the present invention has never been used before.

In one embodiment of the present invention the organism comprising the autologous nucleotide sequences may be subjected to the agent capable of inhibiting the mismatch repair system of the organism in an amount and for a period of time sufficient to reversibly increase the recombination rate between non-identical DNA sequences with that agent. Thus, the second nucleotide sequences which are introduced into the organism comprising the autologous nucleotide sequences are introduced after treating the organism with the agent.

In another particularly preferred embodiment of the present invention the organism is treated with the agent prior, simultaneously and subsequently to introducing the second sequences into the organism with the agent. It is also possible to treat the organism with the agent solely after introducing the second sequences into the organism.

The period of time sufficient to reversibly increase the recombination rate is preferably less than 5 hours, in particular from 0.5 to 5 hours, preferably 1 to 4 hours, and in particular 1 hour.

In the context of the present invention the organism is a eukaryotic, for instance insect, amphibian, animal, mammalian or non-human mammalian organism, or prokaryotic organism, wherein in case the organism is a prokaryotic organism, the organism is an eubacterial or archaeal organism. In a particularly preferred embodiment the eubacterial organism is *Escherichia coli, Streptococcus pneumoniae* or *Salmonella typhimurium*.

In a preferred embodiment of the present invention the agent to be used according to the present invention is a chemical substance or a physical force.

According to the present invention the chemical substance which is particularly preferred is a naturally occurring or synthesized base analogue of naturally occurring nucleotide bases, such as adenine, uridine, cytosine, thymidine or guanidine for instance 2-aminopurine or compounds having the same characteristics such as 2-aminopurine, i.e. being capable of saturating the mismatch repair and/or interacting with enzymes and DNA or nucleotides. A nucleotide sequence, in particular an oligonucleotde, for instance an oligonucleotide comprising mismatched base pairs, or a heteroduplex are, according to the present invention not to be considered as being chemical agents.

Thus, MRS activity may, according to a preferred embodiment of the present invention, be inhibited in cells treated with chemical agents, in particular 2-aminopurine, a base analogue of adenine that mispairs with cytosine. The advantage of chemical inhibition is that it provides for transient inhibition and it can be easily applied to different bacterial species and eukaryotic cells, for instance human or non-human mammalian cells.

According to a particularly preferred embodiment of the present invention the treatment of *Escherichia coli* cells with 2-aminopurine (2-AP) reversibly reduces the efficiency of the mismatch repair system (MRS) by titrating and/or inactivating the MutL protein. The consequence of this transient phenotypic mismatch repair deficiency is a significant increase ($10^4$-fold) in the frequency of recombination between non-identical DNA sequences. This approach has the advantage of simplicity compared to all methods of MRS inhibition/saturation known in the art because it does not require any genetic modification of the used cells. The present invention therefore provides a method for a reversible functional inactivation of the mismatch repair system.

According to a particularly preferred embodiment of the present invention high concentrations of 2-AP cause a mutator effect suggesting a saturation of the MRS. In a preferred embodiment of the present invention 50 μg/ml to 600 μg/ml 2-AP are used. In a further embodiment in particular at least 50 μg/ml, in particular at least 75 μg/ml, at least 100 μg/ml, at least 200 µg/ml, at least 300 µg/ml, at least 400 µg/ml, at least 500 µg/ml or at least 600 µg/ml of 2-AP are used.

The present invention solves the above problem also by providing in a further aspect a process for mutagenizing an organism which process comprises subjecting the organism to conditions allowing homologous recombination between divergent or non-identical DNA sequences present in the organism, subjecting the organism to an agent capable of reversibly saturating or inactivating the MRS of the organism in an amount and for a period of time sufficient to reversibly increase the recombination rate between the non-identical DNA sequences in the organism as described above, and, in a preferred embodiment, removing the agent from the organism.

Thus, the present invention relates to a process for mutagenising an organism which comprises introducing partially homologous DNA sequences into the organism subjecting the organism to conditions allowing homologous recombination between its autologous and the introduced DNA sequences, whereby the organism is subjected to an agent capable of inhibiting the mismatch repair system of the organism in an amount and for a period of time sufficient to reversibly increase the recombination rate between the autologous and the introduced DNA sequences in the organism and, preferably, removing the agent form the organism. As explained above, the non-identical DNA sequences may be genes, operons, gene clusters, chromosomes, plasmids or genomes.

The above process may also be used to increase the recombination rate in an organism as specified above.

Thus, the present invention also relates to a process for the in vivo recombination which comprises combining in a cell a DNA sequence from a first species or genus with the DNA sequence form a second species or genus wherein the first and second DNA sequences have sequences which are partially homologous and have mismatches able to activat the enzymatic mismatch repair system of a cell when said system is functional and wherein the enzymatic mismatch repair system has been inactivated reversibly according to the present invention to enable stable recombination between the first and second DNA sequences thereby, in a preferred embodiment, producing hybrid genes, hybrid genomes, hybrid chromosomes, hybrid operons, hybrid plasmids or hybrid gene clusters. In a preferred embodiment the DNA sequences may be double stranded.

In a preferred embodiment of the above process for recombination the cells of the organism of a first species or first genus are fused to cells of an organism of a second species or second genus to combine in a cell the DNA from the first species or genus with the DNA from a second species or genus and wherein the cells of the organism of the second species or second genus comprise an enzymatic mismatch repair system reversibly inactivated according to the present invention.

In a further preferred embodiment an unicellular organism of a first species or a first genus is crossed with a unicellular organism of a second species or second genus to combine in a cell a DNA sequence from a first species or genus with a DNA sequence from a second species or genus and wherein the enzymatic mismatch repair system of at least one of these organisms has been reversibly inactivated according to the present invention.

In a further preferred embodiment a recipient bacterium of a first species or genus is conjugated or transducted with a donor bacterium of a second species or genus to combine in a cell a DNA sequence from a first species or genus with a DNA sequence from a second species or genus, wherein the donor bacterium has at least one DNA sequence to be transferred to the recipient bacterium and wherein the enzymatic mismatch repair system of at least one of the donor and recipient bacterium is reversibly inactivated according to the present invention.

The invention prefers a further embodiment in which two DNA sequences are placed into a unicellular organism to combine in a cell a DNA sequence from a first species or genus with a DNA sequence from a second species or genus, wherein the organism is reversibly inactivated in its enzymatic mismatch repair system according to the present invention, and wherein the two DNA sequences are partially homologous and derive from two different organisms.

It is particularly preferred to use one of the above processes for recombination, wherein a hybrid gene and/or its encoded protein is produced by selecting the hybrid gene and/or its encoded protein after expression in the organism.

In a preferred embodiment of the above process for recombination each DNA sequence is contained on a separate plasmid and wherein each plasmid is introduced into the organism.

In a particularly preferred embodiment of the present invention the above process for mutagenising an organism or for increasing the recombination rate of an organism forsees that the introduced DNA sequences derive from an organism of a species different to the species of the organism transformed with the introduced DNA sequence. Hence, according to the present invention the introduced nucleotide sequences may derive from a different or also from the same species or even organism as compared to the organism into which the nucleotide sequence is introduced.

In a further preferred embodiment of the present invention the introduced nucleotide sequences are introduced into the organism by natural sex, transduction, conjugational crosses, artificial cell fusion, chemical, physical, electrical or biolistic uptake of the nucleotide sequences.

In a further preferred embodiment of the present invention the homologous recombination between the autologous and the introduced nucleotide sequences involves gene replacement and gene addition.

In a particularly preferred embodiment of the present invention subjecting the organism to the agent capable of inactivating or saturating the MRS takes place prior and/or simultaneously and/or after introduction of the divergent, that means second nucleotide sequences into the organism.

The present invention also provides a process for recombination in vivo of DNA sequences, homologous, but with mismatched bases wherein said sequences are put together in cells or in an organism whose enzymatic mismatch repair system has been reversibly, that means transitorily, inactivated by the transitory application of the agent defined above for a length of time to obtain recombination between said DNA sequences, for instance less than 5 hours, in particular 1 hour.

Thus, the present invention relates to an in vivo process of recombination, that means to a process for the production of recombined organisms by cross, or any other means to put together DNA from different organisms, and recombination in vivo of organism of different species and/or genera, wherein a cross or the other means and a recombination in vivo is carried out between an organism of a first species and/or of a first genus and an organism of a second species and/or of a second genus wherein at least one of these two organisms comprises a reversibly inactivated MRS according to the present invention.

In a particularly preferred embodiment the recombination is a recombination between different species, that means an interspecific recombination or a recombination between organisms of different genuses, that means an intergeneric recombination.

The DNA sequences concerned for recombination may be chromosomic or extra-chromosomal, for instance plasmids, permitting in a particular preferred embodiment recombination between cloned individual genes.

With the above identified process it is possible to produce, in particular genetically engineered or modified, cells or recombined organism of bacteria, yeast, plants or animals.

In a particular preferred embodiment the present invention relates to a process of the production of bacteria recombined by cross and recombination of bacteria of different species and/or genera, wherein a conjugation or transduction is performed in vivo between recipient bacteria of a first species and/or of a first genus, whose enzymatic mismatch system has been reversibly inactivated according to the present invention and donor bacteria of a second species and/or of a second genus which, in a particularly preferred embodiment, comprise a particular trait or property which is desired to be transferred into the recipient bacteria. It is possible to also reversibly inactivate the donor bacteria mismatch repair system according to the present invention using the above identified process and agent.

In a preferred embodiment of the present invention the recipient bacteria are also defective in the enzymatic restriction systems of the DNA.

In a particular preferred embodiment of the above process both strains are crossed in the presence of the agent reversibly inactivating the mismatch repair system and thereafter the agent is removed.

In a particularly preferred embodiment of the present invention a strain of *E. coli* and a strain of *Salmonella typhimurium* are crossed of which at least one, preferably both is/are inactivated according to the present invention in its/ their enzymatic MRS. In an even more preferred embodiment a donor bacterium of the Hfr-type is conjugated with an F⁻-recipient bacterium.

The above identified process of the present invention for the production of recombined organisms or cells, in particular bacteria, is advantageous insofar as it creates new strains of bacteria exhibiting advantageous properties for instance being non-toxic or rendered suitable for the use in the production of vaccines.

The present invention also relates to a process for the production of hybrid genes and their encoded proteins in vivo from two partially homologous genes wherein the recombined cells are prepared from cells of a first organism which contain a first gene and cells of a second organism which contain a second, partially homologous gene, and wherein a process for mutagenesis according to the present invention is carried out in the recombined cell and the desired hybrid gene or its encoded protein is selected therefrom. This process forsees that in an organism comprising an inactivated MRS according to the present invention, two DNA sequences consisting of partially homologous genes deriving from two different organisms are placed together and after in vivo recombination the desired hybrid gene and, if desired, after in vivo protein synthesis the encoded protein is selected. According to a preferred embodiment of this invention at least two plasmids containing at least two partially homologous genes coding for the same function but having a different sequence are introduced into a cell having a reversibly inactivated MRS according to the present invention and, after recombination in accordance with the present invention a hybrid gene and, in a preferred embodiment, after expression uder conventional conditions, the hybrid protein is selected and preferably isolated. The plasmids may be introduced into the organism by conventional transformation methods.

The present invention also relates to a process of targeted inverse mutagenesis of a gene in an organism wherein the gene comprises a mutated base which is desired to be re-established as it was before its mutation, wherein the mismatch repair system of the organism is reversibly inactivated according to the present invention and an oligonucleotide consisting of the DNA sequence to be re-established as it was before mutation is introduced and the re-established mutant is selected from the transformants.

Of course, the present invention is also related to the products obtained according to the processes of the present invention, namely the obtained recombined and/or mutagenised organisms, cells, gene products, proteins, genes, gene clusters, operons, plasmids, chromosomes and genomes.

Further preferred embodiments of the present invention are the subject matter of subclaims.

The invention will now be explained by way of examples and accompanying figures.

The figures show:

FIG. 1: Influence of 2-aminopurine (2-AP) on the efficiency of intraspecies *E. coli* Hfr×*E. coli* F⁻ and interspecies *S. typhimurium* Hfr×*E. coli* F⁻ conjugational recombination. Recipient *E. coli* strains were either mutS⁺ (A, C) or mutS⁻ (B, D). The recombination frequencies for the selected marker (Thr⁺) are expressed per Hfr donor after subtracting unmated revertants. Each number represents the mean (+/− standard error) of at least three independent experiments.

Figure 2:
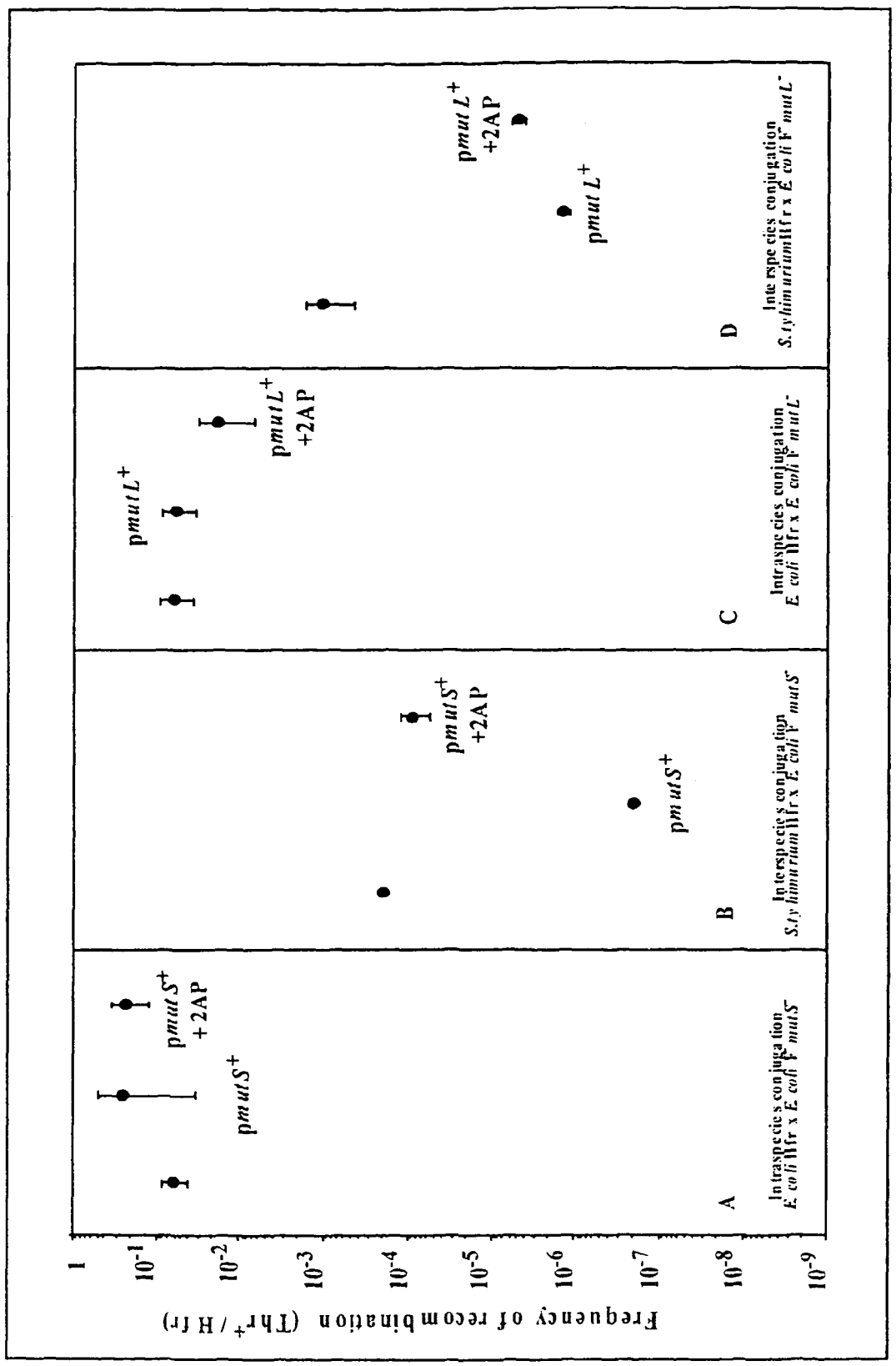

FIG. 2: Identification of the mismatch-repair system component, which is saturated or inhibited with 2-aminopurine (2-AP) treatment. Recipient *E. coli* strains were either mutS⁺ (A, B) or mutL⁻ (C, D). The mismatch repair deficiency was complemented with plasmids carrying mutS⁺ (A, B) or mutL⁺ genes (C, D). The dose of 2-AP used in these experiments was always 300 mg/ml. The recombination frequencies for the selected marker (Thr⁺) are expressed per Hfr donor after subtracting unmated revertants. Each number represents the mean (+/−standard error) of at least three independent experiments.

EXAMPLE

Bacterial Strains, Plasmids, and Culture Conditions

| | Genotype | Reference or source |
|---|---|---|
| Donor strain | | |
| *S. typhimurium* LT2 SA965 | leuBCD39 ara-7 | (Sanderson et al., 1972) |
| *E. coli* K12 P4X | RelA1 spoT1 metB | (Kahn, 1968) |
| MX0 | As P4X, but metB⁺ | |
| Recipient strain | | |
| AB1157 | Thr1 leu6 proA2 his4, thi1 argE3 lacY1 galK2 ara14 xyl5 mtl1 tsx33 str31 supE44 | (Bachmann, 1972) |
| MX1 | As AB1157 but NalR | |
| MX2 | As MX1, but thr-34::Tn10 | thr allele from *E. coli* Genetic Stock Center, Yale University, New Haven, USA |
| MX3 | As AMX1, but Thr-3091::Tn10kan | thr allele from *E. coli* Genetic Stock Center, Yale University, |

-continued

| Genotype | Reference or source |
|---|---|
| MX4 | As MX2, but | New Haven, USA |
|  | _mutS::_Sm-Sp | mutS allele from M. Radman strain collection |
| MX5 | As MX3, but | mutL allete (Pang et al., 1985) |
|  | mutL218::Tn10 |  |
| Plasmids |  |  |
| PMQ341 | mutS+ CamR | (Wu and Marinus, 1994) |
| PMQ339 | mutL+ CamR | (Wu and Marinus, 1994) |

Media:
All strains were cultured at 37° C.
1. LB rich medium: Bacto tryptone (DIFCO) 10 g; Bacto yeast extract (DIFCO) 5 g; NaCl 10 g; Deionized $H_2O$ 1 l. Adjust pH to 7.0 with 1 M NaOH.
2. M63 minimal medium: $KH_2PO_4$ 13.6 g; $(NH_4)_2SO_4$ 2 g; $FeSO_4$ $7H_2O$ 0.5 mg; deionized $H_2O$ 1 l. pH adjusted to 7.0 with KOH. After autoclaving, 1 ml of 1M $MgSO_4$ $7H_2O$ and 10 ml of 20% solution of carbon source was added. Vitamins, amino-acids and antibiotics were added when needed.

When media were used in plates, 15 g agar (DIFCO) of agar was added per litre. All media were sterilized by autoclaving for 30 minutes at 120° C. Antibiotics were always added after autoclaving. Final concentrations of the antibiotic were as follows: nalidixic acid (Sigma), 40 μg/ml; spectinomycin (Sigma), 100 μg/ml; streptomycin (Sigma), 75 μg/ml; kanamycin (Sigma), 50 μg/ml; tetracyclin (Sigma), 12.5 μg/ml; and cloramphenicol (Sigma), 30 μg/ml.

Manipulation of DNA and Microorganisms

Electrotransformation:
Plasmids carrying mutS+ or mutL+ genes were indroduced by electrotransformation (using BIO RAD micro pulser apparatus) in MX4 and MX5 strains, respectively.

Transduction:
All recipient strains were E. coli K12 F− AB1157 strain derivatives that have been constructed using P1 mediated transduction (Miller, 1972).

Conjugational Crosses:
The conjugation experiments have been performed under the previously described conditions (Rayssiguier et al., 1989). The overnight cultures of donor strains ($2-4 \times 10^9$ cells/ml) comprising the DNA sequence to be introduced and recipient strains comprising the autologous DNA sequences were diluted 50-fold into fresh LB medium, with or without 2-aminopurine (Sigma), and grown with gentle shaking (about 150 rpm) in order to obtain $2-4 \times 10^8$ cells/ml. In order to obtain the required concentration of cells, about 3 hours of incubation is required. When cells were treated with 2-AP, the growth was slightly slower (the incubation was about 30 minutes longer) compared to the growth without 2-AP. The 2-AP treatment of the donor and recipient strains before mating is preferred as 2-AP must be incorporated in the DNA during replication in order to saturate mismatch repair. The doses of 2-AP tested were: 25 μg/ml, 50 μg/ml, 75 μg/ml, 100 μg/ml, 300 μg/ml and 600 μg/ml. The effect of 2-AP treatment was already significant when 50 μg/ml of 2-AP was used. The maximal effect was observed at 100 μg/ml of 2-AP, while further increases in 2-AP concentration did not increase further recombination efficiency. Mating mixtures were prepared by mixing together Hfr and F− bacteria in a 1:1 ratio. This mixture was filtered through a sterile 0.45-μm-pore size nitrocellulose filter (2.5 cm diameter), using vacuum filtration equipment (MILLIPORE). The filters with mating mixtures i.e. mixtures with cells comprising autologous and introduced nucleotide sequences were incubated on fresh LB agar plate (with or without 2-aminopurine) prewarmed at 37° C. After 60 min, mating pairs are resuspended in $10^{-2}$ M $MgSO_4$ and separated by vigorous vortexing and thus diluting out 2-AP to inactive levels. Then, the mating mixtures were plated on medium which selected for the desired recombinants (Thr+ phenotype) and counter-selected both donor (Nal$^s$ phenotype) and recipient (Thr− phenotype) parental strains, which do not contain 2-AP. For this purpose, the M9 medium [supplemented with arginine, histidine, leucine, proline and tryptophane (100 μg/ml each), thiamine (30 μg/ml), glucose (0.4%), and nalidixic acid (40 μg/ml) to counter-select the Hfr donor cells] was used. Threonine was not added to the media in order to select Thr+ recombinants. Recombinants were scored after incubation of 48 hours at 37° C.

Results:
The effect of 2-AP treatment on the recombination was demonstrated in the course of the present invention using the well-studied system of conjugational recombination between S. typhimurium×E. coli (Stambuk and Radman, 1998; Rayssiguier et al., 1989; Matic et al., 1995; Denamur et al., 2000). The recombination between these two bacterial species, which have about 16% divergence in their genomic sequences, is very low ($10^{-8}$-$10^{-7}$; FIG. 1A) compared to intraspecies recombination (about $10^{-1}$; FIG. 1C). Inactivation of the mutS or mutL gene in recipient cells according to the present invention using 2-AP increases about $10^3$-$10^4$-fold the frequency of interspecies recombination (FIG. 1B, FIGS. 2A and 2B).

The high recombination rate observed in intraspecies conjugation experiments is not considerably increased by 2-AP treatment in the E. coli system used, both in mutS+ (wildtype) or mutS− background. FIG. 1B shows that in a mutS− recipient background the 2-AP effect is not as pronounced as in a wildtype background (FIG. 1A) since mutS− cells already exhibit high recombination rates due to the MRS having been genetically inactivated (mutS−).

Thus, when wild-type recipient cells have been treated with 75, 100, 300 or 600 μg/ml of 2-AP (an increase of recombination frequency is seen from 50 to 600 μg/ml 2-AP, in particular at and above 75 μg/ml), the frequency of interspecies recombination was increased up to $10^4$-fold, while that of intraspecies recombination was not modified (FIG. 1). By introducing plasmids carrying genes coding for mutS or mutL genes, MutL protein was identified as the component of the MRS, which is titrated or inactivated by the 2-AP treatment (FIG. 2B).

Therefore, it can be concluded that the treatment of E. coli cells with 2-AP results in a transient increase of the recombination efficiency between divergent DNA sequences, in particular by homeologous recombination, by saturating or inhibiting a genetically intact mismatch repair system.

The present invention teaches how to breach genetic barriers particularly in wild type bacteria in a reversible way. Breaching genetic barriers allows for efficient inter-species recombination of genes, operons or genomes producing a novel large-scale biodiversity that can be a useful source of biotechnological innovation. The mechanism of transient increase in interspecies recombination, up to 10.000-fold, is shown in the example above: the chemical substance used, 2-aminopurine, produces a reversible phenotype of DNA mismatch repair deficiency by the depletion the MutL function of the said DNA repair system. The great advantage of this method over the use of mismatch repair deficient mutants is that the genetically unstable state can be strictly limited to the time of interspecies cross: the depletion of the 2-aminopurine brings back the genetic stability. In addition, the present method allows for activation of interspecies recombination also in organisms where the mismatch repair genes are unknown or cannot be genetically manipulated.

REFERENCES

1. Abdulkarim, F., and Hughes, D. (1996). Homologous recombination between the tuf genes of *Salmonella typhimurium*, J Mol Biol 260, 506-522.
2. Bachmann, B. J. (1972). Pedigrees of some mutant strains of *Escherichia coli* K-12, Bacteriol Rev 36, 525-557.
3. Cupples, C., and Miller, J. H. (1989). A set of lacZ mutations in *Escherichia coli* allows rapid detection of each of the six base substitutions, Proc Natl Acad Sci USA 86, 5345-5349.
4. Cupples, C. G., Cabrera, M., Cruz, C., and Miller, J. H. (1990). A set of lacZ mutations in *Escherichia coli* that allow rapid detection of specific frameshift mutations, Genetics 125, 275-280.
5. Denamur, E., Lecointre, G., Darlu, P., Tenaillon, O., Acquaviva, C., Sayada, C., Sunjevaric, I., Rothstein, R., Elion, J., Taddei, F., Radman, M., and Matic, I. (2000). Evolutionary implications of the frequent horizontal transfer of mismatch repair genes, Cell 103, 711-721.
6. Friedberg, E. C., Walker, G. C., and Siede, W. (1995). DNA repair and mutagenesis (Washington, D.C., ASM Press).
7. Kahn, P. L. (1968). Isolation of high frequency recombining strains from *Escherichia coli* containing the V colicinogenic factor, J Bacteriol 96, 205-214.
8. Maas, W. K., Wang, C., Lima, T., Hach, A., and Lim, D. (1996). Multicopy single-stranded DNA of *Escherichia coli* enhances mutation and recombination frequencies by titrating MutS protein, Mol Microbiol 19, 505-509.
9. Matic, I., Rayssiguier, C., and Radman, M. (1995). Interspecies gene exchange in bacteria: The role of SOS and mismatch repair systems in evolution of species, Cell 80, 507-515.
10. Matic, I., Taddei, F., and Radman, M. (1996). Genetic barriers among bacteria, Trends Microbiol 4, 69-73.
11. Miller, J. H. (1972). Experiments in molecular genetics (Cold Spring Harbor, Cold Spring Harbor Laboratory).
12. Pang, P. P., Lundberg, A. S., and Walker, G. C. (1985). Identification and characterization of the mutL and mutS gene products of *Salmonella typhimurium* LT2, J Bacteriol 163, 1007-1015.
13. Petit, M. A., Dimpfl, J., Radman, M., and Echols, H. (1991). Control of chromosomal rearrangements in *E. coli* by the mismatch repair system, Genetics 129, 327-332.
14. Prudhomme, M., Méjean, V., Martin, B., and Claverys, J.-P. (1991). Mismatch repair genes of *Streptococcus pneumoniae*: HexA confers a mutator phenotype in *Escherichia coli* by negative complementation, J Bacteriol 173, 7196-7203.
15. Radman, M., and Wagner, R. (1993). Mismatch recognition in chromosomal interactions and speciation, Chromosoma 102, 369-373.
16. Rayssiguier, C., Thaler, D. S., and Radman, M. (1989). The barrier to recombination between *Escherichia coli* and *Salmonella typhimurium* is disrupted in mismatch-repair mutants, Nature 342, 396-401.
17. Sanderson, K. E., Ross, H., Zeiger, L., and Mäkelä, P. H. (1972). F⁺, Hfr, and F' strains of *Salmonella typhimurium* and *Salmonella abony*, Bact Rev 36, 608-637.
18. Schaaper, R. M., and Radman, M. (1989). The extreme mutator effect of *Escherichia coli* mutD5 results from saturation of mismatch repair by excessive DNA replication errors, EMBO J 8, 3511-3516.
19. Shen, P., and Huang, H. (1989). Effect of base pair mismatches on recombination via the RecBCD pathway, Mol Gen Genet 218, 358-360.
20. Stambuk, S., and Radman, M. (1998). Mechanism and control of interspecies recombination in *Escherichia coli*. I. Mismatch repair, methylation, recombination and replication functions, Genetics 150, 533-542.
21. Vulic, M., Dionisio, F., Taddei, F., and Radman, M. (1997). Molecular Keys to Speciation: DNA Polymorphism and the Control of Genetic Exchange in Enterobacteria, Proc Natl Acad Sci USA 94, 9763-9767.
22. Worth Jr., L., Clark, S., Radman, M., and Modrich, P. (1994). Mismatch repair proteins MutS and MutL inhibit RecA-catalyzed strand transfer between diverged DNAs, Proc Natl Acad Sci USA 91, 3238-3241.
23. Wu, T.-H., and Marinus, M. G. (1994). Dominant negative mutations in the mutS gene of *Escherichia coli*, J Bacteriol 176, 5393-5400.
24. Zahrt, T. C., Mora, G. C., and Maloy, S. (1994). Inactivation of mismatch repair overcomes the barrier to transduction between *Salmonella typhimurium* and *Salmonella typhi*, J Bacteriol 176, 1527-1529.

The invention claimed is:

1. A process for reversibly increasing the recombination rate between a first-DNA sequence and a second DNA sequence in vivo in a prokaryotic organism, wherein the process comprises:
   a) providing to the prokaryotic organism the first DNA sequence obtained from a first species or a first genus and the second DNA sequence obtained from a second species or a second genus, wherein the first and the second DNA sequences, are partially homologous with up to 30% mismatches capable of activating an enzymatic mismatch repair System (MRS) of the prokaryotic organism when the MRS is functional,
   b) subjecting the prokaryotic organism comprising the first and the second DNA sequences to 2-aminopurine in an amount and for a period of time sufficient to inactivate the MRS and thus increase the recombination rate, wherein the period of time is between 1 and 5 hours; and
   c) removing the 2-aminopurine from the prokaryotic organism to reverse the increased recombination rate.

2. The process according to claim 1, wherein the prokaryotic organism is an eubacterial or an archaeal organism.

3. The process according to claim 2, wherein the eubacterial organism is *Escherichia coli*.

4. The process according to claim 1, wherein the first and the second DNA sequences are genes, operons, gene clusters, chromosomes, plasmids or genomes.

5. The process according to claim 1, wherein the first and the second DNA sequences are selected from a naturally occurring and an artificially manipulated DNA sequence.

6. The process according to claim 1, wherein the first and the second DNA sequences are double-stranded.

7. The process according to claim 1, wherein the amount of 2-aminopurine is from 50 ug/ml to 600 ug/ml.

8. The process according to claim 1, wherein the recombination is an intergeneric or an interspecific recombination.

9. The process according to claim 1, wherein in the step of providing to the prokaryotic organism, each DNA sequence is contained on a separate plasmid and wherein each plasmid is introduced into the prokaryotic organism.

10. A process for producing a hybrid gene from the two partially homologous sequences or the encoded protein thereof wherein the process according to claim 1 is carried out and a selection is conducted for the hybrid gene from the two partially homologous sequences or the encoded protein thereof.

11. A process for reversibly increasing the recombination rate between a first DNA sequence and, a second DNA sequence in vivo in a prokaryotic organism, wherein the process comprises
  a) conjugating or transducting a recipient bacterium of a first species or a first genus comprising the first DNA sequence with a donor bacterium of a second species or a second genus comprising the second DNA sequence to produce the prokaryotic organism comprising the first DNA sequence from the recipient bacterium of the first species or the first genus with the second DNA sequence from the donor bacterium of the second species or the second genus, and wherein the first and the second DNA sequences are partially homologous with up to 30% mismatches capable of activating a MRS of the prokaryotic organism when the MRS is functional;
  b) subjecting the recipient bacterium comprising the first and the second DNA sequences to 2-aminopurine in an amount and for a period of time sufficient to inactivate the MRS and thus increase the recombination rate, wherein the period of time is between 1 and 5 hours; and
  c) removing the 2-aminopurine from the recipient bacterium to reverse the increased recombination rate.

12. A process for reversibly increasing the recombination rate between a first DNA sequence and a second DNA sequence in vivo in a unicellular organism, wherein the process comprises
  a) providing the first DNA sequence obtained from a first species or a first genus, and the second DNA sequence obtained from a second species or a second genus to the unicellular organism to combine in the cell the first and the second DNA sequences, wherein the first and the second DNA sequences are from two different organisms, and wherein the first and the second DNA sequences are partially homologous with up to 30% mismatches capable of activating a MRS of the unicellular organism when the MRS is functional;
  b) subjecting the unicellular organism comprising the first and the second DNA sequences to 2-aminopurine in an amount and for a period of time sufficient to inactivate the MRS and thus increase the recombination rate, wherein the period of time is between 1 and 5 hours; and
  c) removing the 2-aminopurine from the unicellular organism to reverse the increased recombination rate.

* * * * *